US007237712B2

(12) United States Patent
DeRocco et al.

(10) Patent No.: US 7,237,712 B2
(45) Date of Patent: Jul. 3, 2007

(54) IMPLANTABLE DEVICE AND COMMUNICATION INTEGRATED CIRCUIT IMPLEMENTABLE THEREIN

(75) Inventors: Paul DeRocco, Pacific Palisades, CA (US); John C. Gord, Venice, CA (US); Einan Regev, Valencia, CA (US); Lawrence J. Karr, Santa Monica, CA (US); Farid David Imani, Valencia, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 175 days.

(21) Appl. No.: 11/002,592

(22) Filed: Dec. 1, 2004

(65) Prior Publication Data

US 2006/0113396 A1    Jun. 1, 2006

(51) Int. Cl.
*G06F 17/00* (2006.01)
(52) U.S. Cl. .................. 235/375; 235/492; 600/546
(58) Field of Classification Search ............... 600/546; 235/472.02
See application file for complete search history.

(56) References Cited

U.S. PATENT DOCUMENTS

| 5,193,539 | A | 3/1993 | Schulman et al. |
| 5,193,540 | A | 3/1993 | Schulman et al. |
| 5,312,439 | A | 5/1994 | Loeb |
| 6,164,284 | A | 12/2000 | Schulman et al. |
| 6,185,452 | B1 | 2/2001 | Schulman et al. |
| 6,208,894 | B1 | 3/2001 | Schulman et al. |
| 6,315,721 | B2 | 11/2001 | Schulman et al. |
| 6,325,294 | B2 * | 12/2001 | Tuttle et al. ................ 235/492 |
| 6,564,807 | B1 | 5/2003 | Schulman et al. |
| 6,643,541 | B2 * | 11/2003 | Mok et al. ................... 600/546 |
| 6,950,842 | B2 | 9/2005 | Kerr |
| 2003/0114897 | A1 * | 6/2003 | Von Arx et al. ............. 607/60 |
| 2003/0144711 | A1 * | 7/2003 | Pless et al. .................. 607/60 |
| 2004/0193090 | A1 | 9/2004 | Lebel et al. |

FOREIGN PATENT DOCUMENTS

| EP | 0 607 638 A | 7/1994 |
| WO | WO 03/053515 A | 7/2003 |
| WO | WO 03/066163 A | 8/2003 |

* cited by examiner

*Primary Examiner*—Seung Ho Lee
(74) *Attorney, Agent, or Firm*—Malcolm J. Romano

(57) ABSTRACT

An implantable device and a wireless communication integrated circuit (IC) implementable in the implantable device for communicating with a remote unit, wherein the communication IC is capable of self-initializing, namely initial booting without requiring an external general booting program to force the booting process. Moreover, the implantable device and the communication IC provide for checking of the validity and integrity of any program instructions received from the remote unit for the desired operation of the implantable device. The implantable device and the communication IC therein have power-saving capability in order to extend the operation of the implantable device between battery charges. A further embodiment provides a robust communication IC, whereby signal distortion or interference between the analog and digital components collectively residing on the same communication IC is minimized or eliminated.

7 Claims, 4 Drawing Sheets

IMPLANTABLE DEVICE AND COMMUNICATION INTEGRATED CIRCUIT IMPLEMENTABLE THEREIN

DETAILED DESCRIPTION OF THE PREFERRED EMBODIMENTS

This description is not to be taken in a limiting sense, but is made merely for the purpose of describing the general principles of the embodiments of the invention. The scope of the invention should be determined with reference to the claims.

The embodiments of the present invention provide an implantable device and a wireless communication integrated circuit implementable in the implantable device for communicating with a remote unit, wherein the communication integrated circuit (IC) is capable of self-initializing, namely initial booting without requiring an external general booting program to force the booting process. As part of the booting process, the IC can automatically download arbitrary program instructions from a remote unit into a program memory. Moreover, the implantable device and the communication integrated circuit provide for checking of the validity and integrity of any program instructions received from the remote unit for the desired operation of the implantable device. The implantable device and the communication IC therein have power-saving capability in order to extend the operation of the implantable device between battery charges. Furthermore, an embodiment of the present invention provides a robust communication IC, whereby the signal distortion or interference between the analog and digital components collectively residing on the same communication IC is minimized or eliminated. The implantable device may be a microelectronic device capable of electrically stimulating body tissue such as nerves and muscles. The microelectronic device may further have the capability to sense body parameters such as electrical signals from nerves/muscles or pressure, temperature and other desired parameters.

Various features and details associated with the manufacture, operation and use of such implantable microelectronic devices may be found in one or more of the following documents, all of which are incorporated herein by reference: U.S. Pat. No. 5,193,539 entitled "Implantable Microstimulator"; U.S. Pat. No. 5,193,540, entitled "Structure and Method of Manufacture of an Implantable Microstimulator"; U.S. Pat. No. 5,312,439 entitled "Implantable Device Having an Electrolytic Storage Electrode"; U.S. Pat. No. 6,164,284, entitled "System of Implantable Devices for Monitoring and/or Affecting Body Parameters"; U.S. Pat. No. 6,185,452, entitled "Battery-Powered Patient Implantable Device"; U.S. Pat. No. 6,208,894, entitled "System of Implantable Devices for Monitoring and/or Affecting Body Parameters"; U.S. Pat. No. 6,315,721, entitled "System of Implantable Devices for Monitoring and/or Affecting Body Parameters"; U.S. Pat. No. 6,564,807, entitled "System of Implantable Devices for Monitoring and/or Affecting Body Parameters".

Figure 1:
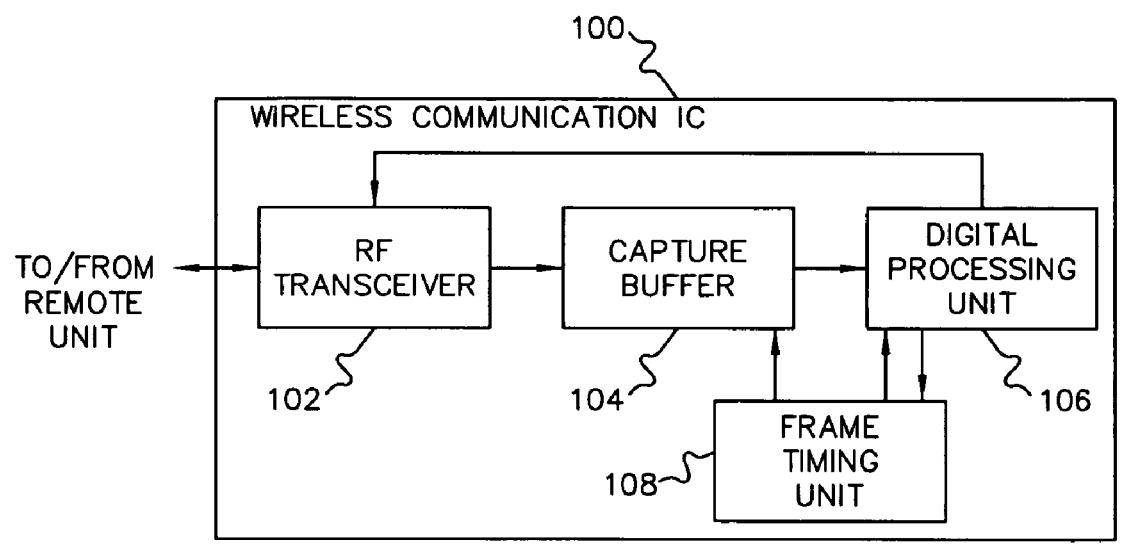
FIG. 1 is an illustration of a block diagram of an embodiment of the general components of a communication IC in accordance with a first embodiment of the present invention.

FIG. 1 illustrates a block diagram of an embodiment of the general components of the communication IC in accordance with the first embodiment of the present invention. The communication IC may be implementable in an electronic device, wherein the electronic device may be a wired or a wireless device. For example, the electronic device may be an implantable device. Referring to FIG. 1, broadly, the communication IC 100 comprises an RF transceiver 102 coupled and communicating with a capture buffer 104 which provides stored digitized communication signals to a digital processing unit 106. In this embodiment of the present invention, it is contemplated that the above-mentioned components collectively reside on the same communication IC 100. The RF transceiver 102 transmits and receives i.e., transceives analog communication signals to/from a remote communication unit and it converts and communicates the received analog communication signals as digitized signals to the capture buffer 104. The digital processing unit 106 comprises various digital components. It is known that because of physical limitations of an integrated circuit in terms of size the components populating the integrated circuit are placed in close proximity to each other, thereby resulting in electrical distortions and crosstalks in the signals processed by the integrated circuit. For example, the analog communication signals received by the RF transceiver 102 may be adversely affected when the components, particularly the digital components, are operating and processing information concurrently with the RF transceiver 102.

It is contemplated that in the present embodiment, the digital processing unit 106 stops operating, for example, stops processing digitized communication signals when the RF transceiver 102 and the capture buffer 104 are communicating. In this manner, for predetermined periods of time when the RF transceiver 102 is receiving analog communication signals and digitizing those signals utilizing an analog-to-digital (A/D) converter for communication/transmission to the capture buffer 104, the digital processing unit 106 and other digital components are stopped from operating. The control of the operation of the digital components is either by virtue of an enable signal halting the operation of relevant digital components or by cutting off power to the relevant digital components utilizing a power distribution unit (described below).

The communication IC 100 further comprises a frame timing unit 108 coupled to the capture buffer 104 and the digital processing unit 106 wherein the frame timing unit 108 synchronizes the operations of the capture buffer 104 and the digital processing unit 106. The frame timing unit 108 effectively operates as a clock/counter and starts the capture buffer 104 operation when its count reaches a predetermined value (corresponding to a frame or series of frames). Then it counts a predetermined number of bits of digitized communication signals received from the RF transceiver 102 and stored in the capture buffer 104 at which time the frame timing unit 108 provides an enable signal to the digital processing unit 106 in order for the digital processing unit 106 to receive the stored digitized communication signals for processing. The digital processing unit 106 sends a signal back to the frame timing unit 108 indicating that it has received all the digitized communication signals from the capture buffer 104. Also, the digital processing unit 106 sets the predetermined value upon which the capture buffer 104 operation will start next time. Moreover, the RF transceiver 102 and the capture buffer 104 are precisely clocked by the same clocking scheme on the communication IC 100 such that the transmission of communication signals from the RF transceiver 102 and the receipt of the same at the capture buffer 104 is substantially simultaneously. This approach prevents or reduces the probability of signal degradation or loss in the communication between the RF transceiver 102 and the capture buffer 104.

Figure 2:
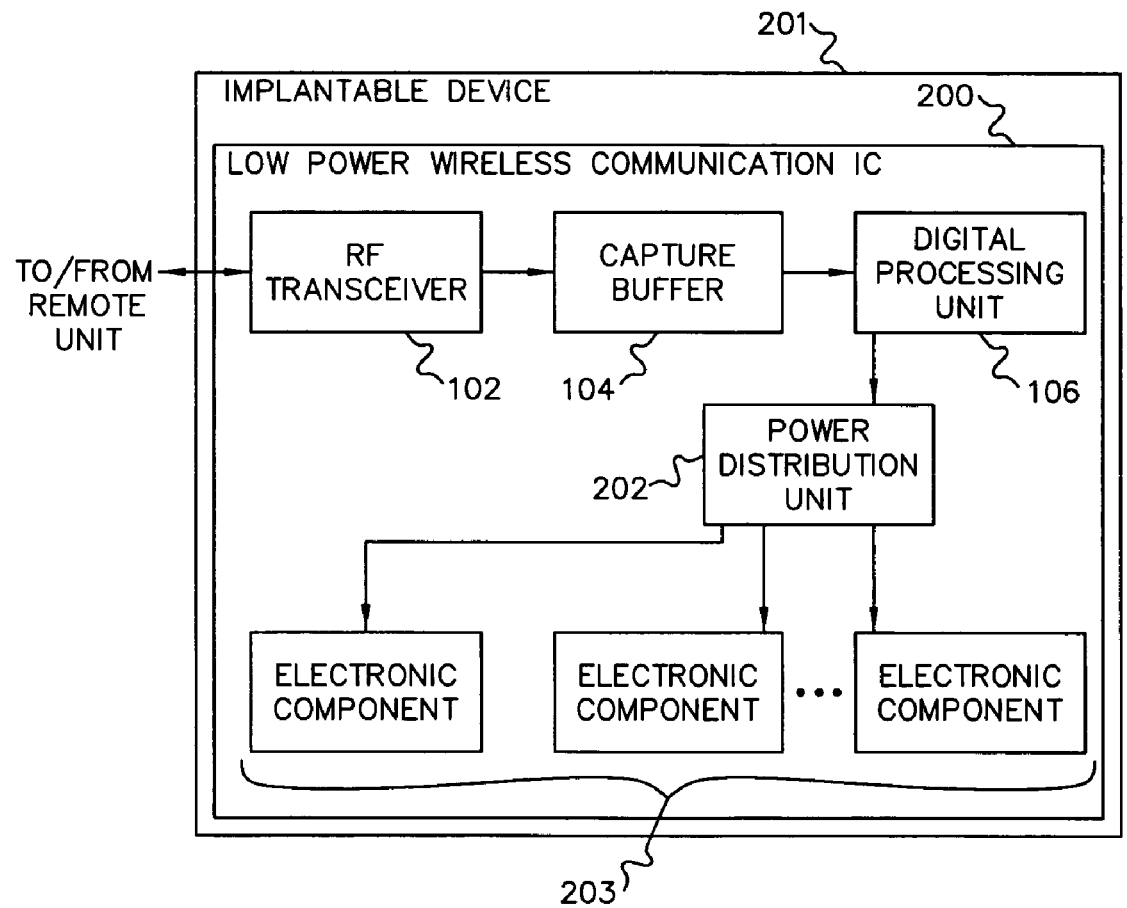
FIG. 2 is an illustration a block diagram of an embodiment of the general components of an implantable device having a low-power communication IC in accordance with a second embodiment of the present invention.

FIG. 2 is an illustration a block diagram of an embodiment of the general components of an implantable device having a low-power communication IC in accordance with the second embodiment of the present invention. Referring to FIG. 2, broadly, the low-power communication IC 200 comprises the RF transceiver 102 coupled and communicating with the capture buffer 104 which provides stored digitized communication signals to the digital processing unit 106, wherein the digital processing unit 106 is coupled to a power distribution unit 202. In the second embodiment of the present invention, it is contemplated that the digital processing unit 106 controls the operation of the power distribution unit 202. The power distribution unit 202 provides power to all of the electronic components 203 on the low-power communication IC 200. Since at various times some of the electronic components 203 may not be performing any operations, then the digital processing unit 106 by controlling the power distribution unit 202 selectively removes power from the electronic components 203, thereby reducing power consumption in the implantable device 201. It should be noted that since the implantable device 201 is battery-powered, any reduction in power consumption provides a longer operating life between recharging cycles of the implantable device 201.

Figure 3:
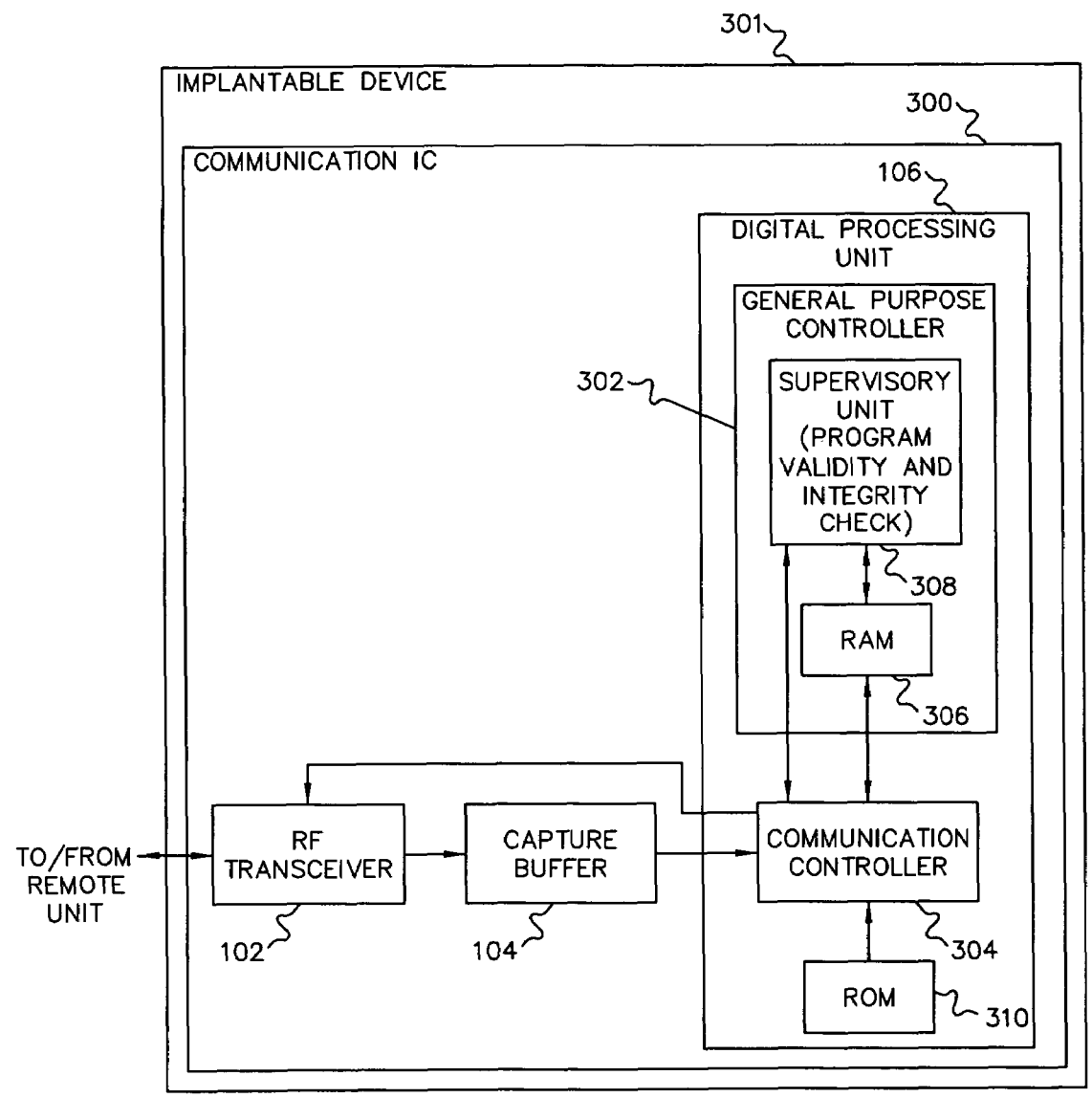
FIG. 3 is an illustration of a block diagram of an embodiment of the general components of an implantable device having a communication IC in accordance with a third embodiment of the present invention.

FIG. 3 is an illustration of a block diagram of an embodiment of the general components of an implantable device having a communication IC in accordance with the third embodiment of the present invention. Referring to FIG. 3, broadly, the communication IC 300 comprises the RF transceiver 102 coupled and communicating with the capture buffer 104 which provides stored digitized communication signals to the digital processing unit 106, wherein the digital processing unit 106 comprises a general purpose controller 302 and a communication controller 304. In the third embodiment of the present invention, it is contemplated that the general purpose controller 302 may be a programmable microprocessor that can run arbitrary code from a Random Access Memory (RAM) 306. The general purpose controller 302 is adapted to receive program instructions from a remote unit for the operation of the implantable device 301 and execution of desired tasks. In the general purpose controller 302, the RAM 306 is loaded with code embodying the program instructions.

A supervisory unit 308 in the general purpose controller 302 performs a reliability check of the program instructions received from the remote unit. The reliability check may be performed through various techniques such as CRC, ARQ, and FEC or any other techniques known to persons skilled in the art. In performing the reliability check, the supervisory unit 308 checks for the sequence of bits received from a remote unit to match the sequence of bits that was actually transmitted by the remote unit. Furthermore, the general purpose controller 302 is adapted to check for the integrity of the program instructions received from the remote unit. By checking the integrity of the program instructions it is meant that the general purpose controller 302 determines whether there are any incorrect programming codes in the received program instructions such as infinite loops or any other forms of programming errors that would hang up a program and possibly result in undesired functions in the implantable device 301. It should be noted that the reliability check and the integrity check functions can be implemented through either hardware or software capabilities in the general purpose controller 302 utilizing designs and techniques known to those skilled in the art. For example, the hardware capabilities may be dedicated logic circuitry. Furthermore, the general purpose controller 302 may include a computer readable medium containing a program having a first executable code wherein the first executable code checks for the reliability of the received program instructions. Furthermore, the computer readable medium may contain a program having a second executable code for checking the integrity of the received program instructions.

In the third embodiment of the present invention, it is further contemplated that the communication controller 304 is adapted for independently initializing and/or enabling the wireless communication operation of the implantable device 301. The communication controller 304 has the capability of initializing, namely booting up the implantable device 301 for the start of communication with a remote unit without requiring access to an external program. The independent boot/initialization means that the communication controller 304 does not need instructions from any external entities or from the general purpose controller 302 in order to boot up from the initialization state to being fully operational and in communication with the remote unit. All necessary parameters needed to establish initial communication with the remote unit reside on an internal Read Only Memory (ROM) 310 and are automatically loaded from the internal ROM 310, whereas other parameters and program codes/instructions are later retrieved from the remote unit after the establishment of initial communication. Finally the program code/instructions of the general purpose controller 302 are downloaded from the remote unit. Moreover, the communication controller 304 acts as a monitor and gateway to the general purpose controller 302 as described below.

Figure 4:
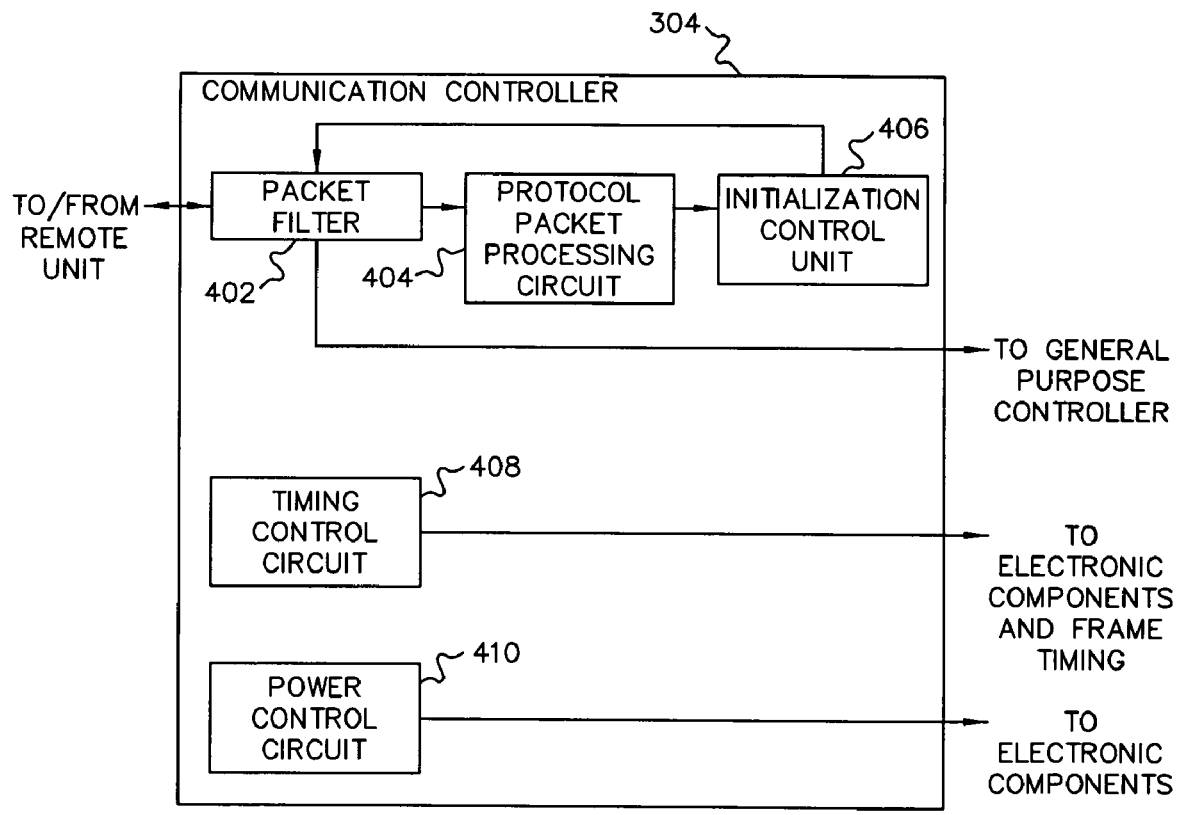
FIG. 4 is an illustration of a communication controller in accordance with an embodiment of the present invention.

FIG. 4 is an illustration of the communication controller in accordance with an embodiment of the present invention. Referring to FIG. 4, the communication controller 304 comprises a packet filter 402, a protocol packet processing circuit 404, an initialization control unit 406, a timing control circuit 408, and a power control circuit 410. The packet filter 402 determines whether the packets of information received are to be processed by the protocol packet processing unit 404 or to be transmitted to the general purpose controller 302. The timing control circuit 408 monitors the timing of the operation of various components and generates timing signals that are provided to, for example, the frame timing unit 108 in order to control the capture operation of the digitized communication signals in the capture buffer 104. The power control circuit 410 communicates with the power distribution unit 202 in order to provide power to or remove power from the electronic components 203 as described above. The initialization control unit 406 controls the process of initialization of the communication controller 304. This process starts at the search mode where there is no existing communication with the remote unit. Once communication is established between the implantable device 301 and the remote unit, the communication controller 304 goes into the track mode, thereby enabling the wireless communication operation of the implantable device 301.

A feature of the third embodiment of the present invention is that the general purpose controller 302 is monitored by the communication controller 304 through the operation of the supervisory unit 308. The supervisory unit 308 periodically checks the validity and integrity of the general purpose controller 302 code. The supervisory unit 308 continually sends the results of these checks to the communication controller 304. When a fault/error is detected, the communication controller 304 immediately disables the general purpose controller 302 from executing further instructions, and notifies the remote unit. The disable condition is maintained until a new program is successfully downloaded into the general purpose controller 302 memory, in which case the disable condition is removed and the general purpose controller 302 resumes execution.

The descriptions of the invention, the specific details, and the drawings mentioned above, are not meant to limit the scope of the present invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes, which come within the meaning and range of equivalency of the claims, are to be embraced within their scope.

What is claimed is:

1. A communication integrated circuit implementable in an electronic device, said communication integrated circuit comprising:
    an RF transceiver for transceiving analog communication signals;
    a capture buffer, communicating with the RF transceiver for predetermined periods of time, wherein the capture buffer receives digitized communication signals from the RF transceiver and stores the digitized communication signals therein;
    a digital processing unit, coupled to the capture buffer, for processing the digitized communication signals, wherein the digital processing unit is adapted to stop operating, when said RF transceiver and said capture buffer are communicating, for the predetermined periods of time, and wherein said RF transceiver, said capture buffer and said digital processing unit collectively reside on said communication integrated circuit.

2. The communication integrated circuit of claim 1, further comprising a frame timing unit coupled to the capture buffer and the digital processing unit wherein the frame timing unit synchronizes the operations of the capture buffer and the digital processing unit.

3. The communication integrated circuit of claim 2, wherein the digital processing unit comprises a communication controller and a general purpose controller.

4. An implantable device having a wireless communication integrated circuit, comprising:
    an RF transceiver for transceiving analog communication signals;
    a capture buffer, communicating with the RF transceiver for predetermined periods of time, wherein the capture buffer receives digitized communication signals from the RF transceiver and stores the digitized communication signals therein;
    a digital processing unit, coupled to the capture buffer, for processing the digitized communication signals, wherein the digital processing unit stops operating when said RF transceiver and said capture buffer are communicating for the predetermined periods of time;
    a power distribution unit, controlled by the digital processing unit, for providing power to electronic components on the communication integrated circuit, wherein the digital processing unit by controlling the power distribution unit selectively removes power from the electronic components when said electronic components are not performing operations, thereby reducing power consumption in the implantable device.

5. The implantable device of claim 4, wherein the digital processing unit comprises a communication controller and a general purpose controller.

6. The implantable device of claim 5, wherein the communication controller is programmed with a predetermined computer program for initializing and/or enabling the wireless communication operation of the implantable device.

7. The implantable device of claim 6, wherein the general purpose controller is adapted to receive computer program instructions from a remote unit for the operation of the implantable device.

* * * * *